United States Patent [19]

Singleton et al.

[11] 3,997,480
[45] Dec. 14, 1976

[54] AIR TREATING GEL

[75] Inventors: Alan Singleton, Glen Waverley; Paul Kemp Montagnat, Langwarrin, both of Australia

[73] Assignee: The Kiwi Polish Company Pty. Ltd., Australia

[22] Filed: Nov. 25, 1974

[21] Appl. No.: 527,168

[52] U.S. Cl. .............................. 252/522; 424/76
[51] Int. Cl.$^2$ ................ A61K 7/46; C11B 9/00
[58] Field of Search ................. 252/522; 424/76

[56] References Cited
UNITED STATES PATENTS

| | | | |
|---|---|---|---|
| 2,927,055 | 3/1960 | Lanzet | 424/76 |
| 3,767,787 | 10/1973 | Segal | 252/522 |

*Primary Examiner*—C. Davis
*Attorney, Agent, or Firm*—Bucknam and Archer

[57] ABSTRACT

An air treating gel comprises an aqueous medium, at least one volatile air treating component and a gelling agent, characterized in that the gelling agent consists of the reaction product of a water soluble cellulose derivative and a metal salt.

The invention also covers an apparatus for continuously producing the above air treating gel comprising a pair of containers holding the aqueous solution of said cellulose derivative and the slurry of said metal salt and said volatile air treating component respectively, mixing means connected to the containers for mixing and reacting the aqueous solution and slurry to form the gel, and transfer means for continuously transferring the aqueous solution and slurry in predetermined volume proportion from the containers to the mixing means.

7 Claims, 1 Drawing Figure

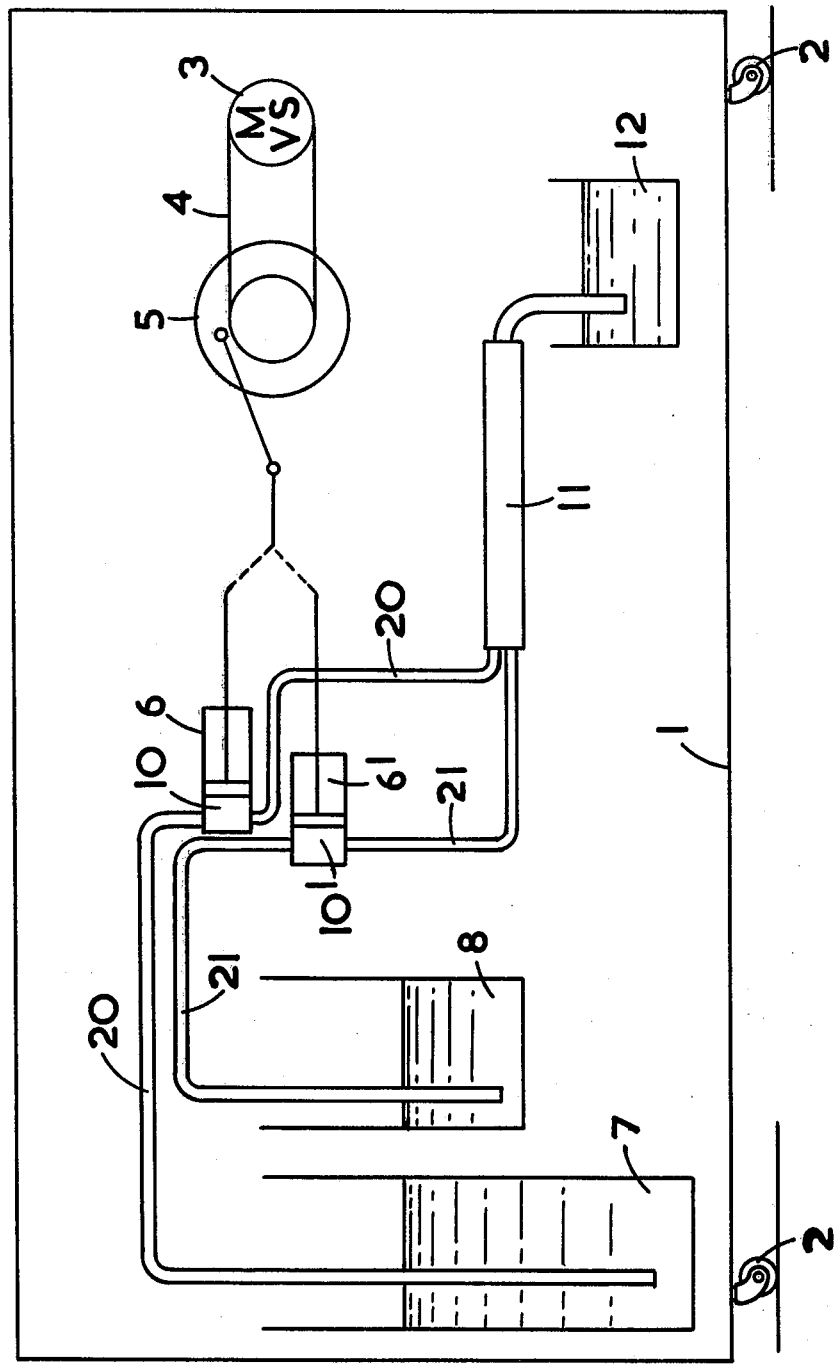

AIR TREATING GEL

This invention relates to air treating gels of the type comprising an aqueous medium, volatile air treating components such as, for example, a reodorant or a perfume, and a relatively small quantity of a gelling agent and is particularly concerned with an improved gelling agent.

Air treating compositions in gel form are known in the art. Air treating materials in this form are particularly easy to handle and are a popular consumer product.

On exposure to air, the aqeuous medium gradually evaporates from the gel, releasing the air treating components into the surrounding atmosphere. These components may include materials such as disinfectants, bactericides, insecticides, and odoriferous perfumes or essential oils which impart a pleasant scent to the atmosphere and/or combat malodors.

Air treating gels of this type are known in the art, for example from U.S. Pat. No. 2,691,615 which teaches the use therein of gelling agents such as alginates, gelatin, pectin, agar-agar, karaya, tragacanth, starch, nitrocellulose compositions, and the like. The gelling agents are characterized in the patent as materials producing gels substantially free of syneresis.

U.S. Pat. No. 2,927,055 teaches an improved gelling agent for use in air treating gels. This agent comprises mixtures of carrageanan, locust bean gum, potassium chloride, and sodium carboxymethyl cellulose in critical proportions. The novel gelling agents are taught to have an advantageous rate of hydration and setting.

There is now world wide shortage of common gelling agents such as mentioned hereinabove and their cost is rising accordingly. Also, in the course of efficient manufacture, most common gelling agents require heating. Thus, it is desirable to make an acceptable air freshener gel using as a base commodity, materials with an assured supply and available at an appreciably lower cost than alternative materials, and which do not require to be heated.

The usual method of manufacture of air treating gels is to manufacture a batch in a vessel at an elevated temperature which is maintained until the container filling process is completed. The air treating gel sets on cooling, typically in a refrigerated tunnel.

It is the principal object of the present invention to provide an air treating gel of the above type containing a gelling agent the use of which is more economical than those hitherto used while at the same time possessing comparable performance, e.g. syneresis properties, thereto.

It is a further object of the present invention to provide a gel of the above type where the gelling reaction takes place at room temperature and no heating with subsequent cooling is required in a continuous process situation.

It is yet another object of this invention to provide an apparatus for producing an air treating gel which apparatus uses a cold filling process wherein a reaction product is produced as required from essentially two reagents which may be prepared previously at a convenient time and stored for use if and when required.

With the above objects in view, the present invention provides an air treating gel comprising an aqueous medium, at least one volatile air treating component and a gelling agent, characterised in that the gelling agent consists of the reaction product of a water soluble cellulose derivative, with or without modifying gums, and a metal salt, preferably a trivalent metal salt having a low solubility in water.

The cellulose derivative is preferably a salt of carboxymethyl cellulose (hereinafter referred to as "CMC"), more preferably an alkali metal salt thereof, such as e.g. sodium CMC.

Preferably, the metal salt is basic aluminium acetate $[(CH_3COO)_4OAl_2 \cdot 4H_2O]$.

The addition of the low solubility metal salt to an aqeuous solution of the cellulose derivative reduces the water solubility of the latter precipitating the metal salt of the cellulose derivative slowly and in controlled manner to form the gel. The above reaction takes place at room temperature and an excess of the cellulose derivative may be used to control syneresis. The cellulose derivative may be used in a concentration of 1 to 10% depending on the viscosity grade of the derivative.

In addition to the essential constituents of the gel composition already listed, the compositions may contain other conventional ingredients such as dyes and preservatives.

In practice, a slurry of the metal salt, volatile component and, optionally, a dye is formed and this is then added to an aqueous solution of the cellulose derivative, optionally in the presence of a preservative, to slowly precipitate the gel at room temperature.

The use of a reaction product involving a cellulose derivative, in conjunction with a metal salt, as the gelling agent is relatively economical. Furthermore, as the reaction to form the gelling agent take place at room temperature, no time-consuming cooling step is required and the gel may thus be produced in a continuous process.

EXAMPLE 1

9130 g of water were added to a 15 litre stainless steel vessel fitted with an electrically driven stirrer. The stirrer speed was adjusted to given an efficient agitation of the water and 300 g of sodium carboxymethyl cellulose were added carefully into the vortex formed by the stirrer.

The rate of addition of the sodium carboxymethyl cellulose was such that no lumping or aggregation of the small particles occurred when in the water phase. Such lumping or aggregation could occur if the sodium carboxymethyl cellulose was added too quickly and sufficient time not allowed for smooth and efficient dispersion of the particles. The time taken for this addition in the present example was three minutes. 20 g of a preservative was added to the contents.

The contents of the steel vessel were stirred for a further 30 minutes, by which time a smooth clear viscous paste had formed. This solution will be called

Solution A.

Into a separate vessel fitted with an electrically driven stirrer were charged 400 g of a preferred reodorant oil and 1 g of a preferred green dye in water.

These materials were mixed by stirring and 50 g of powdered basic aluminium acetate were added slowly over 1 minute to the stirred mixture. A viscous slurry of basic aluminum acetate dispersed in the reodorant oil/dye solution was formed, and this will be called Solution B.

A mechanical device consisting essentially of two synchronously metering pumps was constructed whereby the two pumps could deliver volumes of liquid in the ratio of approximately 17:1 respectively on each complete cycle of the pump operation. An essential feature was that the pumps operated in phase with each other. Each pump was of the reciprocating-piston type.

This mechanical device was capable of being driven by hand or, more preferably, could be connected to a suitable form of electrical power supply.

The outlets of the two pumps were connected to an in-line mixer.

In this example, Solution A was poured into a reservoir which supplied the larger of the two pumps and Solution B was connected to the smaller pump.

On each cycle of the pumps, the required quantities of Solutions A and B were delivered into the mixer such that the emergent product was of uniform colour and smooth consistency.

Each cycle of the pumps also produced enough finished product to fill a suitable, e.g. plastic, container in which the product would be used for its intended purpose as an air treating gel.

After 30 minutes the product had begun to take on a gel-like character and after a further 30 minutes a non-pourable gel was obtained.

EXAMPLE 2

This example serves to illustrate that the water-soluble gum does not have to be confined to a single viscosity grade. Several viscosity grades are commercially available from several manufacturers and any combination of these grades is allowed within the limitations imposed by such constraints as maximum practical viscosity that can be handled by the aforementioned pump and economic considerations.

In this example, 9030 g of water were charged to the 15 litre steel vessel and stirred vigorously as in Example 1.

A mixture of 300 g of sodium carboxymethyl cellulose, high viscosity grade and 100 g of sodium carboxymethyl cellulose, low viscosity grade was added carefully to the water so that no lumping or aggregation occured. After about 30 minutes stirring a smooth homogeneous viscous paste was obtained.

20 g of preservative were added and stirred into the paste.

This solution is now equivalent to Solution A of Example 1. Solution B was prepared in an identical manner so that of Example 1 and the manufacturing procedure of that example was followed exactly.

The aforementioned preferred processes described in the Examples hereinabove may be performed using the following preferred apparatus described with reference to the accompanying drawing.

A strong rigid frame 1 is mounted on four wheels 2 to provide mobility. An electric motor 3 of variable speed is mounted on the frame 1 and is connected to a suitable drive mechanism 4 for a cam wheel 5. The cam wheel 5 is eccentrically connected to a pair of synchronously operating pistons 6, 6' of different bore sizes and can be adjusted to give greater or lesser eccentricity and so shorten or lengthen the stroke of the pistons 6, 6' connected to it, thereby adjusting the fill volume.

The perfume — metal salt slurry and the aqueous solution of CMC are in containers 7 and 8 respectively, these being connected by pipes 20 and 21 respectively to the piston housings 9, 9' which, apart from the pistons 6, 6', also house valve arrangements 10, 10', conveniently in the form of non-return ball valves, for metering the solution and slurry in predetermined proportions to an in-line mixer 11 through said pipes 20 and 21. The in-line mixer is connected with reservoir 12 which serves to store the finished gel composition and allow completion of the reaction between the reactants. Reservoir 12 may be conveniently the ultimate container in which the product is marketed.

The pistons 6, 6' pump their liquid in unison through their valve arrangements effectively metering predetermined proportionate amounts per stroke on account of the different bore sizes of the pistons.

After being metered through the valve arrangement 10, 10', the reagent liquids meet at the beginning 11a of the in-line mixer 11. As the reagent liquids are pushed into the in-line mixer 11, the preceding reagents are mixed and reacted in the in-line mixer 11 and are forced out into the container 12 at the end of the mixer in the required amount.

The pipe 20 from the CMC container 7 to the valve arrangement 10 in the piston housing 9 may be of reinforced plastic or metal to reduce cavitation. The pipe 21 into the slurry valve arrangement 10' from container 8 can be reinforced if desired. Between the valves and the mixer, the tube should be rigid to eliminate swelling or surging effects due to pumping action.

The claims defining the invention are as follows:

1. An air treating gel consisting essentially of an aqueous medium, at least one volatile air treating component and a gelling agent, wherein the gelling agent consists of the reaction product of a water soluble alkali metal salt of carboxymethyl cellulose and a trivalent metal salt having low solubility in water.

2. The air treating gel according to claim 1 wherein said cellulose derivative is a sodium salt of carboxymethyl cellulose.

3. An air treating gel as claimed in claim 1 wherein said trivalent metal salt is basic aluminium acetate $[(CH_3COO)_4OAl_2.4H_2O]$.

4. A process for producing the air treating gel of claim 1 comprising reacting a slurry of metal salt and said volatile air treating component with an aqueous solution of the cellulose derivative to precipitate the gel.

5. A process as claimed in claim 4 wherein the reaction takes place at ambient temperature.

6. A process for continuously producing the air treating gel of claim 1 comprising continuously withdrawing the slurry of the metal salt and volatile component on the one part and the aqueous solution of the said alkali metal salt of carboxymethyl cellulose on the other part by means of a pair of synchronously operating pumps having capacities in a ratio corresponding to the volumes of slurry and solution required to react, continuously feeding said slurry and solution by means of said pumps through a valve arrangement to an in-line mixer in said volume ratio, and reacting said slurry and solution to form the gel.

7. A process as claimed in claim 6 wherein said metal salt is basic aluminium acetate $[CH_3COO)_4OAl_2.4H_2O]$.

* * * * *